United States Patent
Lakios et al.

(10) Patent No.: US 10,149,983 B2
(45) Date of Patent: Dec. 11, 2018

(54) SKIN TANNING AND PHOTOTHERAPY SYSTEM AND APPARATUS

(71) Applicants: Seoul Viosys Co., Ltd., Ansan-si (KR); Sensor Electronic Technology, Inc., Columbia, SC (US)

(72) Inventors: Emmanuel Lakios, Mount Sinai, NY (US); Max Shatalov, Columbia, SC (US); Timothy Bettles, Irmo, SC (US); Alex Dobrinsky, Loudonville, NY (US)

(73) Assignees: Seoul Viosys Co., Ltd., Ansan-si (KR); Sensor Electronic Technology, Inc., Columbia, SC (US)

( * ) Notice: Subject to any disclaimer, the term of this patent is extended or adjusted under 35 U.S.C. 154(b) by 211 days.

(21) Appl. No.: 15/187,214

(22) Filed: Jun. 20, 2016

(65) Prior Publication Data
US 2017/0361125 A1    Dec. 21, 2017

(51) Int. Cl.
*A61N 5/06* (2006.01)

(52) U.S. Cl.
CPC ......... *A61N 5/0614* (2013.01); *A61N 5/0616* (2013.01); *A61N 2005/0615* (2013.01); *A61N 2005/0626* (2013.01); *A61N 2005/0637* (2013.01); *A61N 2005/0651* (2013.01); *A61N 2005/0659* (2013.01); *A61N 2005/0661* (2013.01); *A61N 2005/0662* (2013.01)

(58) Field of Classification Search
CPC ................ A61N 5/0614; A61N 5/0616; A61N 2005/0615; A61N 2005/0626; A61N 2005/0637; A61N 2005/0651; A61N 2005/0659; A61N 2005/0661; A61N 2005/0662
USPC ......................................... 607/91, 88, 90, 94
See application file for complete search history.

(56) References Cited

U.S. PATENT DOCUMENTS

| | | | | |
|---|---|---|---|---|
| 5,725,565 A | * | 3/1998 | Smith | A61N 5/0614 368/10 |
| 2005/0085877 A1 | * | 4/2005 | Kratz | A61B 5/0059 607/94 |
| 2007/0276455 A1 | * | 11/2007 | Fiset | A61C 19/066 607/91 |

* cited by examiner

*Primary Examiner* — Michael Carey
(74) *Attorney, Agent, or Firm* — H.C. Park & Associates, PLC (57) ABSTRACT

A tanning or a phototherapy system including a light source including light emitting elements configured to emit ultraviolet (UV) light having different peak wavelengths, a controller configured to control luminous characteristics of the light source, and a sensor configured to sense at least one of the luminous characteristics of the light source and a user's skin condition, in which the luminous characteristics of the light source are controlled by the controller based on the user's skin condition sensed by the sensor, and controlling the luminous characteristics comprises increasing or decreasing luminous intensity of one or more of the light emitting elements.

22 Claims, 10 Drawing Sheets

SKIN TANNING AND PHOTOTHERAPY SYSTEM AND APPARATUS

BACKGROUND

Field

Exemplary embodiments relate to a tanning or phototherapy system and apparatus and, more particularly, to a tanning or phototherapy system and apparatus capable of providing various tanning or phototherapy effects.

Discussion of the Background

Generally, tanning or skin tanning refers to darkening of the skin through exposure to sunlight in order to obtain a desired skin color tone and increase individuality. Various tanning apparatuses are being developed to allow users to enjoy tanning effects indoors, regardless of season or time.

Ultraviolet (UV) radiation is generally categorized into three wavelength ranges, in particular, UVA, UVB, and UVC. UVA wavelengths are known to have the greatest influence on skin tanning. UVA wavelengths induce generation of melanin pigment in the skin, which causes a tanning phenomenon in the skin. Although UVB wavelengths generally reach up to the epidermis of the skin, the UVB wavelengths may harm DNA of a cell through direct reaction with the DNA of the cell. Accordingly, an artificial tanning apparatus is generally configured to emit UVA light while minimizing UVB light.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a tanning or phototherapy system and apparatus that includes a light source, which may be automatically or manually controlled according to a user, thereby providing optimal tanning or phototherapy effects.

Additional aspects will be set forth in the detailed description which follows, and, in part, will be apparent from the disclosure, or may be learned by practice of the inventive concept.

According to an exemplary embodiment of the present invention, a tanning system includes a light source including light emitting elements configured to emit ultraviolet (UV) light having different peak wavelengths from one another, a controller configured to control luminous characteristics of the light source, and a sensor configured to sense at least one of the luminous characteristics of the light source and a user's skin condition, in which the luminous characteristics of the light source are controlled by the controller based on the user's skin condition sensed by the sensor, and controlling the luminous characteristics comprises increasing or decreasing luminous intensity of one or more of the light emitting elements.

According to an exemplary embodiment of the present invention, a tanning apparatus includes a body having a tanning space therein, a light source configured to emit ultraviolet (UV) light to the tanning space, the light source including light emitting elements configured to emit UV light having different peak wavelengths, a controller configured to control luminous characteristics of the light source, and a sensor configured to sense at least one of the luminous characteristics of the light source and a user's skin condition, in which the luminous characteristics of the light source are controlled by the controller based on the user's skin condition sensed by the sensor, and controlling the luminous characteristics comprises increasing or decreasing luminous intensity of one or of the more light emitting elements.

According to an exemplary embodiment of the present invention, a phototherapy system includes a light source including light emitting elements configured to emit UV light having different peak wavelengths, a controller configured to control luminous characteristics of the light source, and a sensor configured to sense at least one of the luminous characteristics of the light source and a user's skin condition, in which the luminous characteristics of the light source are controlled by the controller based on the user's skin condition sensed by the sensor, and controlling the luminous characteristics includes increasing or decreasing luminous intensity of one or more of the light emitting elements.

The foregoing general description and the following detailed description are exemplary and explanatory and are intended to provide further explanation of the claimed subject matter.

BRIEF DESCRIPTION OF DRAWINGS

The accompanying drawings, which are included to provide a further understanding of the inventive concept, and are incorporated in and constitute a part of this specification, illustrate exemplary embodiments of the inventive concept, and, together with the description, serve to explain the principles of the inventive concept.

DETAILED DESCRIPTION OF THE ILLUSTRATED EMBODIMENTS

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

A tanning system, a tanning apparatus and a phototherapy system according to exemplary embodiments of the invention can be realized in various ways.

Although various exemplary embodiments illustrated herein are described with reference to a tanning system and apparatus, however, it should be understood that the present disclosure is not limited thereto. For example, exemplary embodiments of the present invention may also be applied to a phototherapy system and apparatus substantially within the same or equivalent range. Further, exemplary embodiments of the present invention may also be applied to light emitting devices using UV light.

Figure 1:
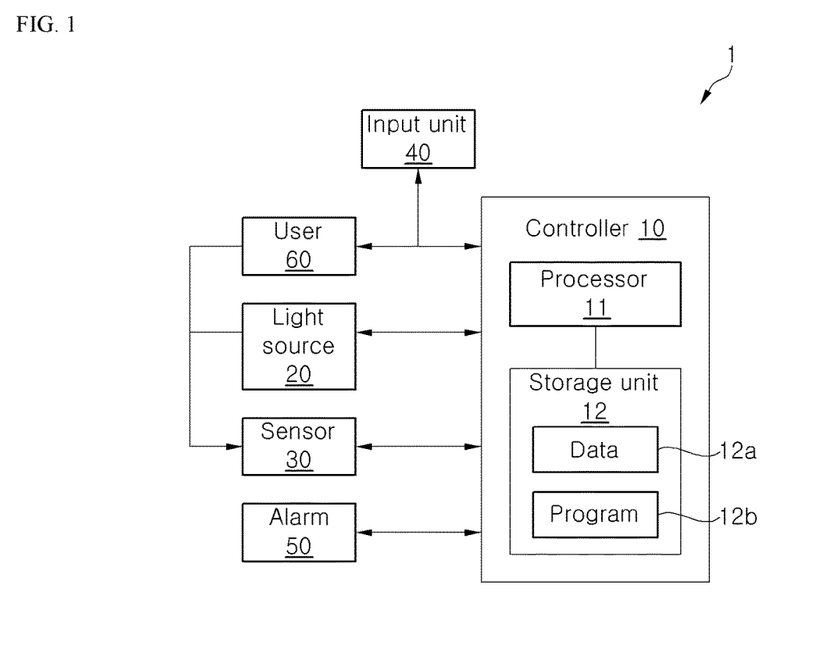
FIG. 1 is a block diagram of a tanning system according to an exemplary embodiment of the present invention.

FIG. 1 is a block diagram of a tanning system according to an exemplary embodiment of the present invention.

Referring to FIG. 1, a tanning system 1 includes a controller 10, a light source 20, and a sensor 30. The tanning system 1 may further include an input unit 40 and an alarm 50. The tanning system 1 may be controlled by the controller 10 through input, control, or a user feedback.

The controller 10 may control various operations of the tanning system 1, and include a processor 11 and a storage unit 12. The processor 11 may be associated with controlling the entire controller 10, and may execute various operations and processes with respect to data input to the controller 10. For example, the processor 11 may output commands to control the light source 20 and/or the alarm 50, based on a series of data input by a user and/or the sensor 30. This will be described in more detail below.

The storage unit 12 may include data 12a and a program 12b. The data 12a may include data previously input to a storage device of the storage unit 12 and real-time data input during the operation of the tanning system 1. The program 12b allows the processor 11 to execute a predetermined command or process based on the data 12a input through a solution or algorithm thereof.

The data 12a may include control data with respect to the light source 20 according to a user, control data with respect to the alarm 50 according to a user, and control data with respect to the light source 20 and the alarm 50 according to data obtained from the sensor 30. The data 12a may be converted into other mechanical instructions through a solution or algorithm of the program 12b and sent to the processor 11. More particularly, the processor 11 may control the light source 20, the alarm 50, and the sensor 30, based on data transmitted from the storage unit 12.

The light source 20 may include a typical lamp, a light emitting diode, and the like. According to the present exemplary embodiment, the light source 20 of the tanning system 1 may include at least one UV light emitting diode. The light source 20 may emit light in various wavelength bands. For example, the light source 20 may emit UVA light having a wavelength of about 320 nm to about 400 nm. The light source 20 may also emit UVB light having a wavelength of 320 nm or less. According to an exemplary embodiment of the present invention, the light source 20 may be configured to emit a mixed light including 95% or more of UVA light and 5% of less of UVB light. In this manner, the tanning system 1 may prevent a user from being harmed by the UVB light. A ratio of UVB light/UVA light may vary from, for example, 0.02 to 0.1.

Luminous characteristics of the light source 20 may be modified in various ways. The luminous characteristics may include at least one of wavelengths of light emitted therefrom, luminous intensity depending upon wavelengths, luminous spectrum of light, and irradiation time of light. The luminous characteristics of the light source 20, that is, the wavelengths, intensity and spectrum of light, and time may be controlled by the controller 10. The controller 10 may control the luminous characteristics of the light source 20 based on data obtained from the data 12a of the storage unit 12 and the program 12b. The data 12a input to the storage unit 12 may include data input by a user, data input through the input unit 40 by a user or a third party, and data input from the sensor 30.

The light source 20 may include multiple light emitting elements, which may be individually controlled so as to modify luminous characteristics of light emitted therefrom. Controlling at least one of the luminous characteristics of the light source 20 may include increasing or decreasing luminous intensity of one or more light emitting elements, such as setting on/off for one or more of the light emitting elements.

The light source 20 may include light emitting elements configured to emit UVA light in the wavelength band of 320 nm to 400 nm and having different peak wavelengths. As used herein, having different peak wavelengths may refer to, for example, an interval between peak wavelengths of light is set to be substantially constant with one another. The controller 10 may increase or decrease luminous intensity of each of the UV light emitting diodes. For example, the light source 20 may include first to seventh UV light emitting diodes having peak wavelengths of 320 nm, 325 nm, 330 nm, 340 nm, 350 nm, 360 nm, and 370 nm, respectively. The first to seventh UV light emitting diodes may be individually controlled by the controller 10, and the intensity and luminous spectrum of light emitted from the light source 20 are controlled by controlling the luminous intensity of each of the first to seventh UV light emitting diodes.

In particular, the luminous characteristics of the light source 20 may be adjusted in various ways by increasing or decreasing the luminous intensity of one or more light emitting elements. Since the wavelength, spectrum, and overall intensity of light may be easily controlled by adjusting the luminous characteristics of one or more light emitting elements, the tanning system 1 according to the exemplary embodiments of the present invention may provide light specialized according to a user 60, without a complex solution or a complex circuit design. In addition, since the UV light emitting diodes may have a narrower full width at half maximum (FWHM) than typical mercury lamps, the UV light emitting diodes having different peak wavelengths may be utilized as the light emitting elements, such that the luminous characteristics of the light source 20 may be easily adjusted by adjusting the luminous characteristics of each of the UV light emitting diodes.

For example, a person having darker skin may require UVA light having a shorter wavelength than a person having lighter skin upon tanning. More particularly, irradiation with UVA light having a shorter wavelength may provide higher tanning effects to a person having yellow or brown skin than a person having white or light yellow skin. On the contrary, a person having lighter skin may more easily suffer from sunburn than a person having a darker skin. Although sunburn is generally caused by UVB light, UVA light may also cause sunburn. As such, a person having lighter skin may have a higher frequency of sunburn by UVA light than a person having a darker skin. More particularly, there are various tanning conditions that may provide optimal tanning effects according to a user while minimizing harm. According to exemplary embodiments of the present invention, the tanning system 1 includes the light source 20 configured to provide UV light having different wavelengths, intensities, and luminous spectra according to a user 60, thereby improving tanning effects while minimizing harm to the user 60.

The light source 20 may further include at least one light emitting element that emits IR (infrared) light and/or visible light. The tanning system 1 according to exemplary embodiments of the present invention may provide phototherapy effects through the at least one light emitting element emitting IR light and/or visible light.

The sensor 30 senses at least one luminous characteristics of the light source 20 and/or at least one user's skin conditions. The luminous characteristics of the light source 20 may be controlled according to the user's skin conditions sensed by the sensor 30. The luminous characteristics of the light source 20 and/or the user's skin conditions obtained from the sensor 30 are sent to the controller 10, which in turn may output a corresponding command to the light source 20.

The light source 20 may be controlled by the controller 10 based on the data 12a previously input by a user 60. A user 60 may provide the data 12a with respect to a user's skin type and a desired degree of tanning to the controller 10 through the input unit 40. The controller 10 may determine optimal luminous characteristics of the light source 20 based on the data 12a, and control the light source 20 to be operated according to the determined luminous characteristics. For example, when a user selects and inputs the user's skin photo-type and a desired degree of tanning, the program 12b may calculate control data with respect to the light source 20 that corresponds to the selected skin photo-type and the degree of tanning, based on the data 12a of the storage unit 12, which are sent to the processor 11. Then, the processor 11 may control the luminous characteristics of the light source 20, such that the user 60 may achieve a desired tanning result.

According to an exemplary embodiment of the present invention, the light source 20 may be controlled by the controller 10 based on the data 12a input on real-time basis from the sensor 30. The sensor 30 senses user's skin conditions. The sensor 30 may contact or be separated from a user's skin for sensing the user's skin conditions. The user's skin conditions sensed by the sensor 30 may include at least one of skin color, melanin concentration, skin sebum, skin moisture, skin temperature, skin trouble, and the like. The sensor 30 may include, for example, a corneometer, a hydrometer, a Tewameter, a sebumeter, a skin-pH-meter, an optical meter, a thermometer, a spectrocolorimeter, a camera, and the like. For example, when a user 60 utilizes the tanning system 1, the sensor 30 senses user's skin conditions in real-time. Then, the real-time sensed skin condition data is to the controller 10 and constitute the data 12a of the storage unit 12. The controller 10 determines optimal luminous characteristics of the light source 20 based on the data 12a, thereby providing an optimal tanning result.

For example, the sensor 30 continues to sense a user's skin color, which is one of the user's skin conditions, using the tanning system 1. When melanin pigment is generated in the user's skin as tanning proceeds, the sensor 30 detects the change of the user's skin color and allows the controller 10 to control the light source 20 to change both the intensity and the wavelength of UV light to achieve the target tanning characteristics. For instance, the intensity and wavelength of UV light can be correlated with user's skin color at set time intervals during tanning to achieve target tanning characteristics. In addition, the duration of the tanning may be adjusted based on user's skin color and his preferences for tanning. In addition, when it is determined that the degree of tanning is sufficient based on the user's skin color detected by the sensor 30, the controller 10 may turn off the light source 20 or decrease the luminous intensity of the light source 20.

The sensor 30 may further sense luminous characteristics of light emitted from the light source 20. For example, the sensor 30 may sense the characteristics of light emitted from the light source 20 by measuring the spectrum of light emitted from the light source 20, in order to monitor whether luminous characteristics intended by the controller 10 are being implemented. When the light source 20 includes multiple light emitting elements, the sensor 30 may sense each of the light emitting elements. Data of the luminous characteristics sensed by the sensor 30 are sent to the controller 10, which in turn may determine defects in the light source based on the data of the luminous characteristics of the light source 20. When some of the light emitting elements have defects, the controller 10 may operate an alarm function, such that the light emitting elements having defects may be replaced.

The sensor 30 may include a camera to photograph a user's skin. The camera may photograph a portion or the entirety of the user's skin while the user utilizes the tanning system 1, to provide data on user's skin conditions.

According to an exemplary embodiment of the present invention, the light source 20 may be controlled by the controller 10 based on both data previously input by a user and data sent from the sensor 30 on a real-time basis. More particularly, the light source 20 may be controlled by the controller 10 based on the data 12a previously input by a user 60, according to the data 12a sent from the sensor 30 in real-time. For example, a user 60 may input the data 12a with respect to a desired degree of tanning to the controller 10 through the input unit 40. When the user 60 uses the tanning system 1, the sensor 30 senses the user's skin conditions in real-time and sends the sensed user's skin condition data to the controller 10, and the data sent from the sensor 30 partially constitutes the data 12a of the controller 10. As such, the data 12a of the controller 10 may include the data input by a user 60 and the skin conditions data sent from the sensor 30, such that the controller 10 may determine optimum luminous characteristics of the light source 20 based on the data 12a, thereby providing an optimal tanning result while minimizing harm to the user's skin.

The input unit 40 may receive various data and commands. The data and commands input to the input unit 40 may be sent to the controller 10 and constitute data. The input unit 40 may include a display and/or an input device. The alarm 50 may be connected to the controller 10 to send various signals to a user. For example, the alarm 50 may send a warning alarm signal, a tanning time completion alarm signal, or an abnormal skin response alarm signal to a user. The alarm 50 may send such signals to a user in various ways, for example, through a visual stimulus and/or an audible stimulus.

Figure 2:
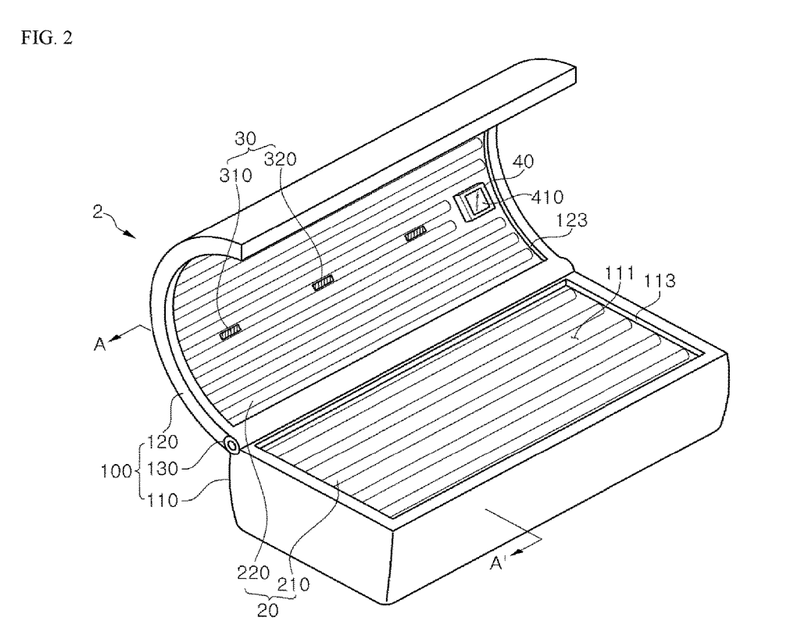
FIG. 2 is a perspective view of a tanning apparatus according to an exemplary embodiment of the present invention.
Figure 3:
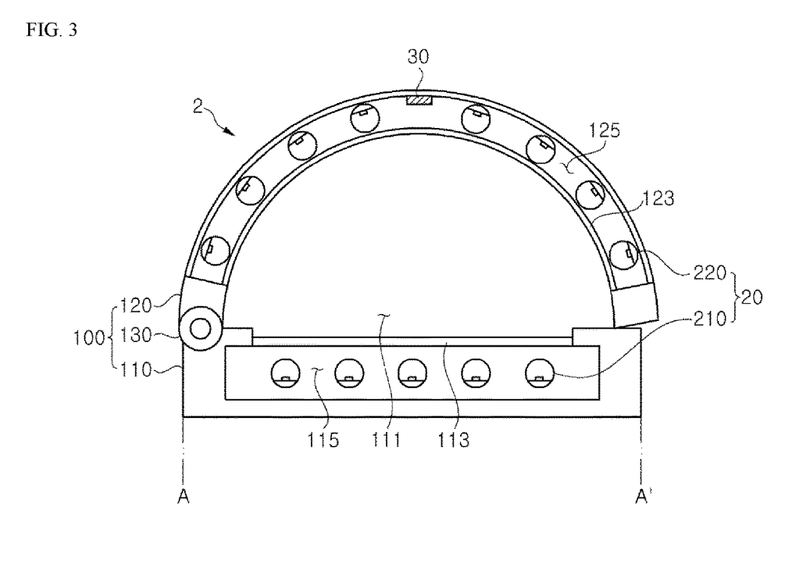
FIG. 3 is a sectional view of a tanning apparatus according to an exemplary embodiment of the present invention.

FIG. 2 is a perspective view of a tanning apparatus according to an exemplary embodiment of the present invention. FIG. 3 is a cross-sectional view of the tanning apparatus taken along line A-A' of FIG. 2. The tanning system illustrated with reference to FIG. 1 may be applied to the tanning apparatus of FIG. 2 and FIG. 3.

Referring to FIG. 2 and FIG. 3, a tanning apparatus 2 according to the present exemplary embodiment includes a controller (not shown), a body 100, light sources 20, and a sensor 30. The tanning apparatus 2 may further include an input unit 40 and an alarm (not shown).

The body 100 may include a lower body 110 and an upper body 120. The body 100 may further include a connector 130 that connects the lower body 110 to the upper body 120.

The body 100 may include a tanning space 111 in which a user may be placed for tanning effect. The tanning space 111 may be placed on the lower body 110, and the upper body 120 may be disposed to surround a portion of the tanning space 111. It is contemplated that, however, a structure of the body 100 may be varied as long as the body 100 provides the tanning space. For example, the lower body 110 may alternatively have a substantially flat upper surface to define a space in which a user may lie, and the upper body 120 may have a concave space downwardly open to surround the tanning space 111.

Each of the lower body 110 and the upper body 120 may include a light source installation space 115 and/or 125, to which the light sources 20 are provided, respectively. Each of the lower body 110 and the upper body 120 may include a light source cover 113 and/or 123 disposed between the light source 20 and the tanning space 111. The light sources 20 may be disposed in the installation spaces 115 and 125 of the lower body 110 and the upper body 120, and light emitted from the light source 20 is discharged to the tanning space 111 through the light source covers 113 and/or 123.

The light source covers 113 and 123 may be formed of a light transmissive material, specifically a UV light transmissive material, more specifically a UVA light transmissive material. For example, the light source covers 113 and 123 may include at least one of TEFLON Teflon™, fluorinated ethylene propylene (FEP), polytetrafluoroethylene (PTFE), ethylene chlorotrifluoroethylene (ECTFE), polychlorotrifluoroethylene (PCTFE), perfluoroalkoxy (PFA), polyvinylidene fluoride (PVDF), ethylene tetrafluoroethylene (ETFE), ethylene propylene copolymer (EFEP), copolymer of tetrafluoroethylene, hexafluoropropylene, and vinylidene fluoride (THV), and copolymer of hexafluoropropylene, tetrafluoroethylene, and tetrafluoroethylene (HTE). THV is a copolymer containing tetrafluoroethylene, hexafluoropropylene and vinylidenefluoride. THV is melt-processible with melting points from 240° to 455° F. (115° to 235° C.) depending on grade. THV is available in pellet, agglomerate, or aqueous dispersions. HTE is a copolymer of hexafluoropropylene, tetrafluoroethylene, and ethylene. HTE is melt-processible with melting points from 310° to 420° F. (155° to 215° C.) depending on grade, and is available in pellet or agglomerate form. The light source covers 113 and 123 may be formed of solid material and/or mesh-formed material. The light source covers 113 and 123 may protect the light sources 20 from external environments while improving luminous uniformity of light emitted from the light sources 20. For example, the light source covers 113 and 123 may include light scattering particles, such as zirconium oxide ($ZrO_2$), titanium oxide ($TiO_2$), and the like, to improve luminous uniformity and luminous efficacy of light passing through the light source covers 113 and 123.

The light source covers 113 and 123 may further include filters that block light having wavelengths harmful to the human body, for example, filters that block UVB light and/or UVC light. The light source covers 113 and 123 may also include at least one of silicone, urethane, polystyrene, polycarbonate, polyethylene terephthalate (PET), polymethylmethacrylate resins, lead glass, soda lime glass, borosilicate glass, quartz and fluorinated polymers (e.g., TEFLON™, FEP, PTFE, ECTFE, PCTFE, PFA, PVDF, ETFE, EFEP, THV, HTE, etc.).

The connector 130 may connect or fasten the lower body 110 to the upper body 120. The connector 130 may allow the upper body 120 to be opened or closed through a rotation thereof. The connector 130 may alternatively have various shapes.

The controller (not shown) may be disposed outside or inside the body 100. The controller may include a processor and a storage unit. The controller may include various integrated circuit (IC) chips constituting the processor and the storage unit. The controller may be connected to at least one of the light sources 20, the sensors 30, the input units 40, and an alarm to allow bi-directional transmission of data. The controller may perform generally similar operations and functions as that described with reference to FIG. 1.

The light sources 20 may include at least one lower light source 210 and at least one upper light source 220. The lower light source 210 may be disposed at an upper portion of the lower body 110 or inside the lower body 110, and the upper light source 220 may be disposed at an upper portion of the upper body 120 or inside the upper body 120. As shown in FIG. 3 the lower light source 210 and the upper light source 220 may be disposed in the light source installation spaces 115 and 125 of the lower body 110 and the upper body 120, respectively.

The lower light source 210 and the upper light source 220 may emit UV light, more particularly, light with 95% or more of UVA light. The lower light source 210 and the upper light source 220 may include light emitting elements emitting light having different wavelengths. Hereinafter, the lower light source 210 and the upper light source 220 will be described in more detail with reference to FIG. 4 to FIG. 9.

Figure 4:
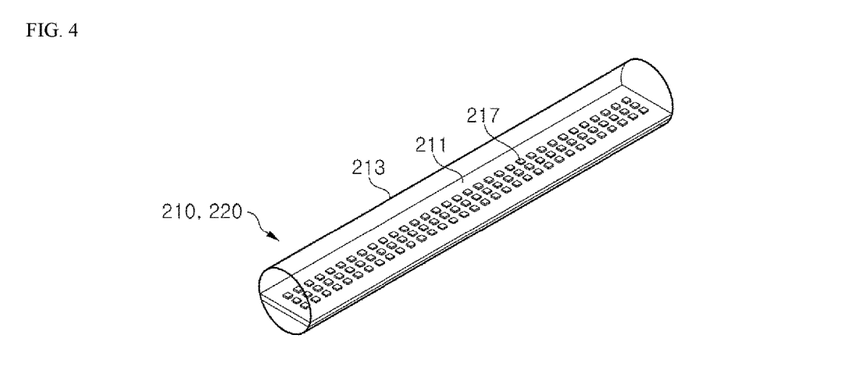
FIG. 4 and FIG. 5 are a perspective view and a plan view of light emitting elements according to exemplary embodiments of the present invention, respectively.
Figure 5:
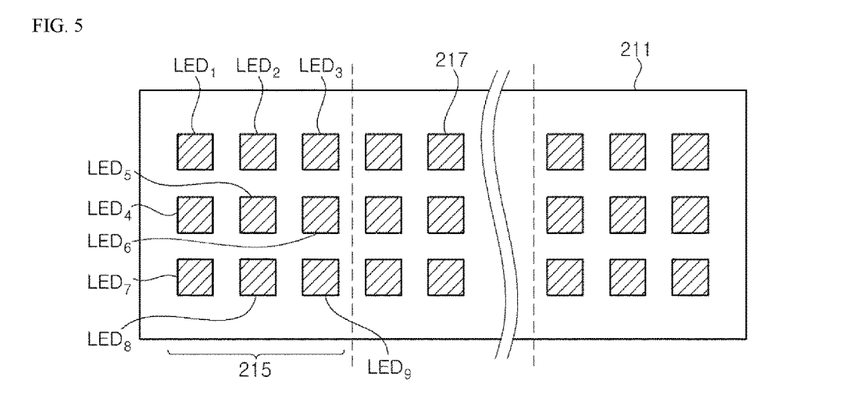

Referring to FIG. 4 and FIG. 5, at least one of the lower light source 210 and the upper light source 220 includes light emitting elements 217, a substrate 211 on which the light emitting elements 217 are disposed, and a cover unit 213.

At least one of the lower light source 210 and the upper light source 220 may have an elongated shape extending in one direction, and the cover unit 213 may have a cylindrical shape or a polygonal column shape. The substrate 211 may provide a region on which the light emitting elements 217 are disposed, and may have any shape so long as the substrate 211 may be electrically connected to the light emitting elements 217. For example, the substrate 211 may include a printed circuit board (PCB). The cover unit 213 may include a light transmissive material and allow light emitted from the light emitting elements 217 to pass therethrough.

The light emitting elements 217 may include UV light emitting diodes LED1 to LED9 having different peak wavelengths. The peak wavelengths of the UV light emitting diodes LED1 to LED9 may have a substantially constant interval therebetween. For example, the UV light emitting diodes LED1 to LED9 include first to ninth UV light emitting diodes LED1 to LED9. The peak wavelengths of the first to ninth UV light emitting diodes LED1 to LED9 are set to have a substantially constant peak wavelength. By way of example, the first UV light emitting diode LED1 emits light having a peak wavelength of about 316 nm, the second UV light emitting diode LED2 emits light having a peak wavelength of about 322 nm, the third UV light emitting diode LED3 emits light having a peak wavelength of about 328 nm, the fourth UV light emitting diode LED4 emits light having a peak wavelength of about 334 nm, the fifth UV light emitting diode LED5 emits light having a peak wavelength of about 340 nm, the sixth UV light emitting diode LED6 emits light having a peak wavelength of about 346 nm, the seventh UV light emitting diode LED7 emits light having a peak wavelength of about 352 nm, the eighth UV light emitting diode LED8 emits light having a peak wavelength of about 358 nm, and the ninth UV light emitting diode LED9 emits light having a peak wavelength of about 364 nm.

On/off or luminous intensity of each of the first to ninth UV light emitting diodes LED1 to LED9 may be independently controlled by the controller. In this manner, the intensity and luminous spectrum of light in the wavelength band of about 316 nm to 364 nm may be changed depending upon the wavelengths of light. Accordingly, the controller may easily control the luminous characteristics of the light source 20 based on user purposes and user's skin condition data sent from the sensor 30. Although the light emitting elements 217 are described as to include nine UV light emitting diodes having different wavelengths, it is contemplated that, however, any types and numbers of UV light emitting diodes having any peak wavelengths may be utilized.

The light sources may include at least one light emitting unit 215 including one or more light emitting elements 217. The light emitting unit 215 may include UV light emitting diodes having different peak wavelengths. For example, as shown in FIG. 5, at least one of the lower light source 210 and the upper light source 220 may include light emitting units 215. The light emitting units 215 include the first to ninth UV light emitting diodes LED1 to LED9. In this manner, the light emitting units 215 may individually emit light having various luminous spectra. The light emitting units 215 may be arranged on the substrate 211 along an extending direction of the substrate 211. More particularly, the light emitting units 215 having substantially the same UV light emitting diodes may be uniformly arranged on the substrate 211 in general, thereby forming a uniform luminous pattern over a light emitting plane, even when the lower light source 210 and the upper light source 220 have an elongated shape. At least one of the lower light source 210 and the upper light source 220 may alternatively include two or more light emitting units 215 capable of realizing luminous characteristics.

The light emitting elements 217 may be disposed on at least one of the lower light source 210 and the upper light source 220 in various ways. For example, a distance between light emitting elements 217 of adjacent light emitting units 215 may be substantially the same as a distance between adjacent light emitting elements 217 of the same light emitting unit 215.

Figure 6A:
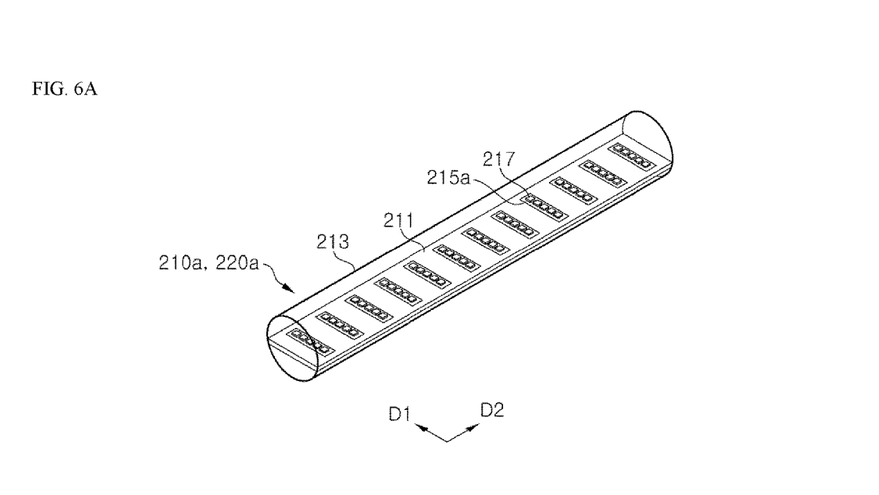
FIG. 6A, FIG. 6B, and FIG. 6C are perspective views of light emitting elements according to exemplary embodiments of the present invention.
Figure 6B:
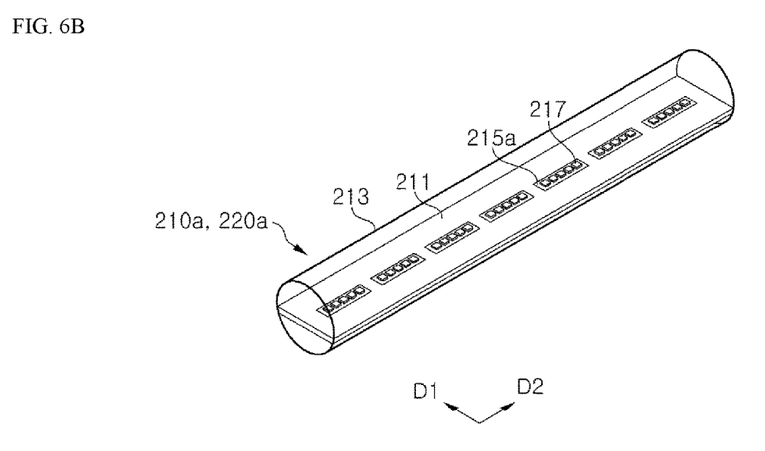
Figure 6C:
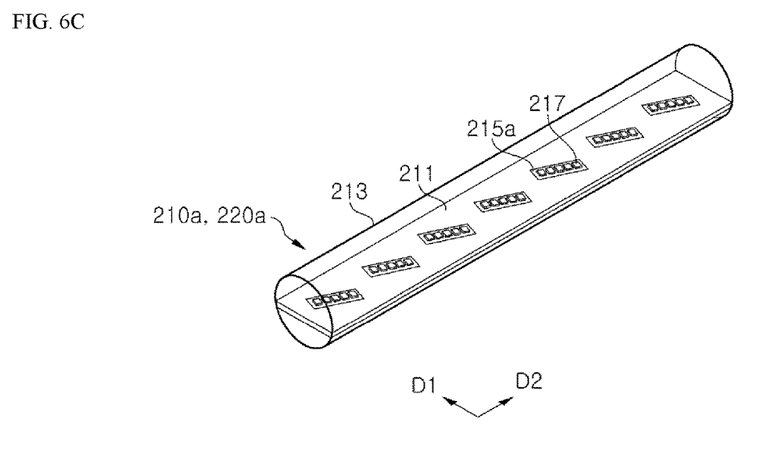
Figure 7:
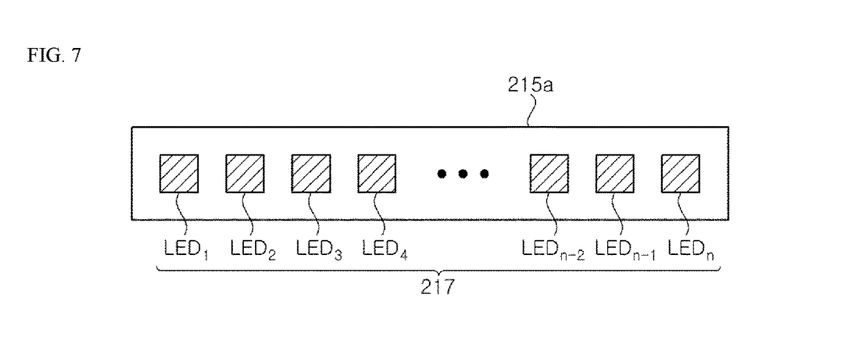
FIG. 7 is a plan view of light emitting elements according to an exemplary embodiment of the present invention.

FIG. 6A to FIG. 6C are perspective views of a lower light source 210a and an upper light source 220a according to an exemplary embodiment of the present invention. FIG. 7 is a plan view of light emitting units 215a according to an exemplary embodiment of the present invention.

Referring to FIG. 6A to FIG. 6C, at least one of the lower light source 210a and the upper light source 220a includes light emitting units 215a separated from each other. Unlike the light emitting units 215 illustrated with reference to FIG. 4 and FIG. 5, in which the light emitting units 215 are defined by dividing the uniformly arranged light emitting elements 217 to constant regions, the light emitting units 215a according to the present exemplary embodiment are arranged at constant intervals.

Referring to FIG. 7, each of the light emitting units 215a may include light emitting elements 217 each including a first UV light emitting diode LED1 to an n-th UV light emitting diode LEDn. Peak wavelengths of the first to n-th UV light emitting diode LED1 to LEDn have a substantially constant difference therebetween. The first to n-th UV light emitting diodes LED1 to LEDn are arranged in an extending direction of the light emitting units 215a. Although the first to n-th UV light emitting diode LED1 to LEDn are described as generally being arranged along a line, it is contemplated that, however, the UV light emitting diodes may be arranged in various shapes, for example, along two or more lines.

The first to n-th UV light emitting diodes LED1 to LEDn of the light emitting units 215a may be directly mounted on the substrate 211 or on a separate submount. More particularly, each of the light emitting units 215a may include a submount, which is mounted on the substrate 211.

The light emitting units 215a having an elongated shape extending in one direction may be arranged on the substrate 211 in various directions. Referring back to FIG. 6A to FIG. 6C, direction D1 refers to a horizontal direction with respect to the extending direction of the lower light source 210a and the upper light source 220a, direction D2 refers to a direction perpendicular to direction D1 and horizontal to short sides of the lower light source 210a and the upper light source 220a. As shown in FIG. 6A, the light emitting units 215a may be generally arranged along direction D2. Alternatively, as shown in FIG. 6B, the light emitting units 215a may be generally arranged along direction D1. Alternatively, as shown in FIG. 6C, the light emitting units 215a may be generally arranged along a direction different from direction D1 and direction D2.

The arrangement direction of the light emitting units 215a may be varied by taking into account the density of light emitted from the lower light source 210a and the upper light source 220a, manufacturing costs, and the like. For example, arrangement of the light emitting units 215a as illustrated with reference FIG. 6A may provide light having high density.

Figure 8:
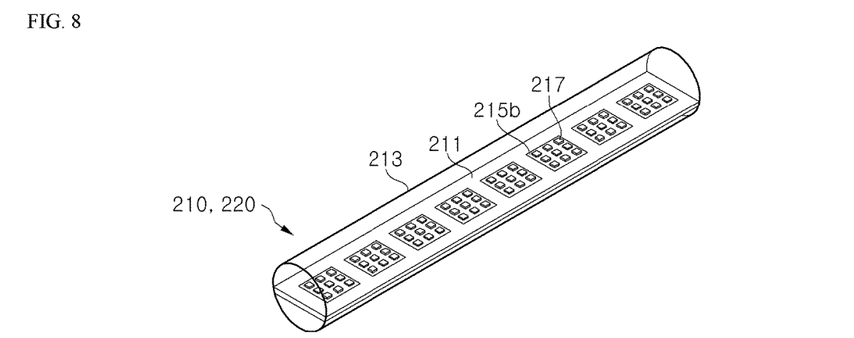
FIG. 8 and FIG. 9 are a perspective view and a plan view of light emitting elements according to exemplary embodiments of the present invention, respectively.
Figure 9:
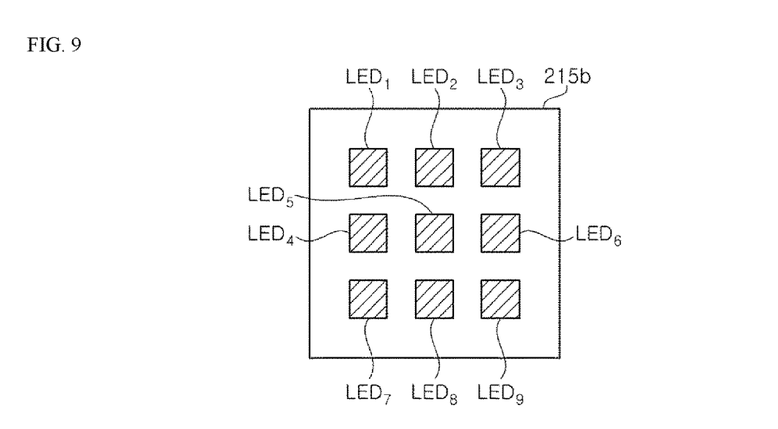

FIG. 8 is a perspective view of a lower light source 210b and an upper light source 220b according to an exemplary embodiment of the present invention. FIG. 9 is a plan view of light emitting units 215b according to an exemplary embodiment of the present invention.

Referring to FIG. 8, at least one of the lower light source 210b and the upper light source 220b includes light emitting units 215b separated from each other. Unlike the light emitting units 215 illustrated with reference to FIG. 4 and FIG. 5, in which the light emitting units 215 are defined by dividing the uniformly arranged light emitting elements 217 to constant regions, the light emitting units 215b according to the present exemplary embodiment are arranged at constant intervals. Referring to FIG. 9, each of the light emitting units 215b may include light emitting elements 217, and each light emitting unit 215b includes a first UV light emitting diode LED1 to an n-th UV light emitting diode LEDn. The light emitting units 215b may generally have a square shape. Peak wavelengths of the first to n-th UV light emitting diode LED1 to LEDn may have a substantially constant difference therebetween. The first to n-th UV light emitting diodes LED1 to LEDn are generally arranged in a uniform pattern.

The first to n-th UV light emitting diode LED1 to LEDn of the light emitting units 215b may be directly mounted on the substrate 211 or on a separate submount. More particularly, each of the light emitting units 215b may include a submount, which is mounted on the substrate 211.

Figure 10:
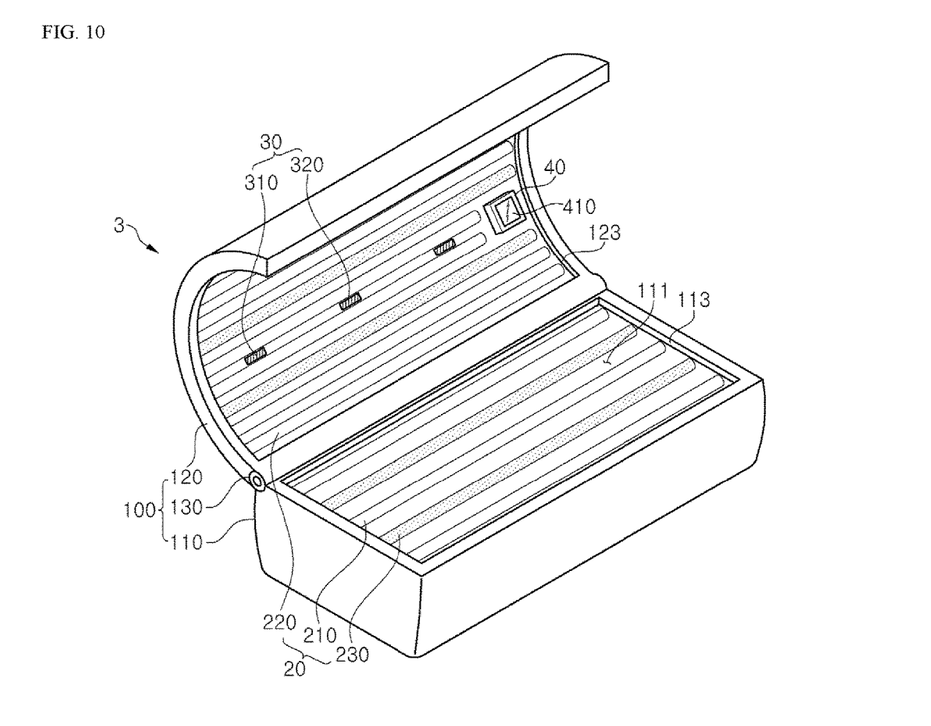
FIG. 10 is a perspective view of a tanning apparatus according to an exemplary embodiment of the present disclosure.

Referring to FIG. 10, the light source 20 may further include an additional light source 230 configured to emit light having other wavelengths, instead of UV light. More particularly, the light source 20 of the tanning apparatus 3 may further include an additional light source 230 disposed in at least one of light source installation space 115 or 125 of the lower body 110 and the upper body 120. The additional light source 230 may emit at least one of IR light and visible light. In this manner, the tanning apparatus 3 may be used as an IR treatment apparatus or provide a skin relaxation effect during tanning, by utilizing IR light emitted from the additional light source 230. Further, the tanning apparatus 3 may have an aesthetically pleasing appearance by utilizing visible light emitted from the additional light source 230.

According to an exemplary embodiment of the present invention, the tanning apparatus 3 may diagrammatically visualize the tanning procedure implemented therein from the outside, by regulating the color sense of visible light emitted from the additional light source 230. For example, the additional light source 230 may emit visible light that may provide relatively cold feeling (for example, blue-based color) while tanning with relatively low intensity and emit visible light that may provide relatively hot feeling (for example, red-based color) while tanning with relatively high intensity.

Referring back to FIG. 2 and FIG. 3, the lower light source 210 and the upper light source 220 may have at least one shape of the lower light source and the upper light source illustrated with reference to FIG. 4 to FIG. 9. The lower light source 210 and the upper light source 220 may be disposed to extend in a horizontal direction with respect to a longitudinal side of the lower body 110.

The sensor 30 may be disposed on at least one of the lower body 110 and the upper body 120. For example, the sensor 30 may be disposed on an upper surface of the lower body 110 and/or on a lower surface of the upper body 120 constituting the tanning space 111. As shown in the drawings, the sensor 30 may be disposed on the lower surface of the upper body 120 to sense at least one skin conditions of a user lying inside the tanning space 111 and/or at least one luminous characteristics of light emitted from the light source 20. The sensor 30 may include multiple sensors. For example, as shown in the drawings, the sensor 30 may include a first sensor 310 and a second sensor 320, which sense different characteristics.

The sensor 30 may alternatively be disposed outside the body 100. In this manner, the user's skin conditions are first sensed by the sensor 30 before tanning of a user, and tanning is performed under control of the controller. The sensor 30 may include one or more sensors, for example, a corneometer, a hydrometer, a Tewameter, a sebumeter, a skin-pH-meter, an optical meter, a thermometer, a spectrocolorimeter, a camera, a smart skin sensor, and the like.

The sensor 30 may contact or be separated from a user's skin when sensing the user's skin conditions. For example, the sensor 30 may be a light transmissive smart skin sensor, which may be attached to the cover 113 of the lower body 110 so as to directly contact the user's skin to sense the user's skin conditions.

The input unit 40 includes an input device configured to allow a user to input data. The input unit 40 may be disposed on an inner surface of the lower body 110 or the upper body 120, such that a user may input data before tanning, during tanning, or after tanning. The input unit 40 may alternatively be disposed outside the lower body 110 or the upper body 120. The input unit 40 may further include a display device, such that a user may monitor a current operation state of the tanning apparatus 2, current skin conditions, and the like in real-time through the display device. For example, the input unit 40 may include a device enabling input and display operation, such as a touchscreen 410.

An alarm (not shown) may be provided to the lower body 110 or the upper body 120. For example, the alarm may include a lamp that provides a visual stimulus to a user and/or a speaker that provides an audible stimulus to a user. The alarm may be connected to the controller.

Figure 11:
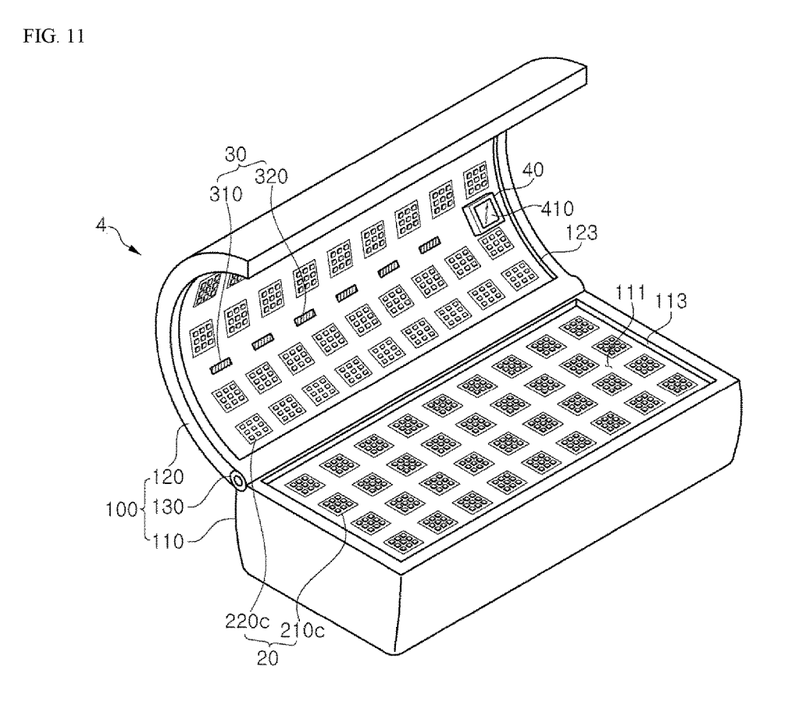
FIG. 11 is a perspective view of a tanning apparatus according to an exemplary embodiment of the present invention.
Figure 12:
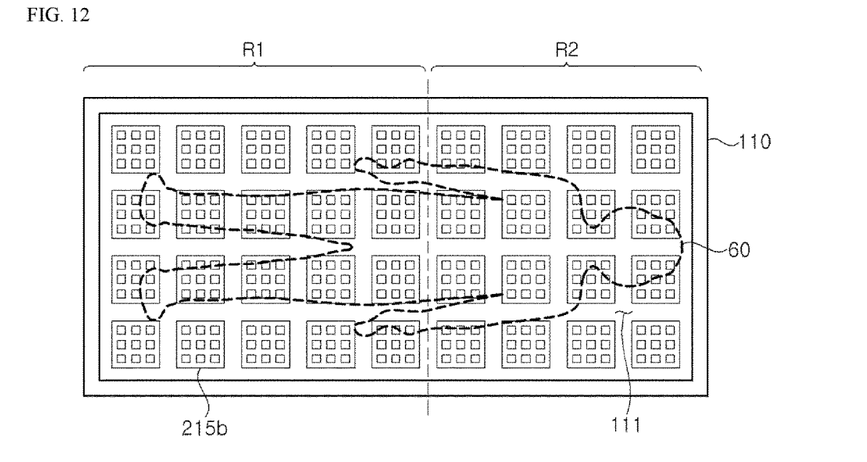
FIG. 12 is a plan view of the tanning apparatus according to an exemplary embodiment of the present invention.

FIG. 11 is a perspective view of a tanning apparatus according to an exemplary embodiment of the present invention. FIG. 12 is a plan view of the tanning apparatus according to an exemplary embodiment of the present invention.

Unlike the tanning apparatus illustrated with reference to FIG. 2 and FIG. 3, the tanning apparatus according to the present exemplary embodiment includes light emitting regions R1 and R2 emitting light having different luminous characteristics. Operations and constituent elements of the tanning apparatus 4 may be substantially similar to those of the tanning apparatus illustrated above, and thus, different features of the tanning apparatus 4 will be mainly described below and repeated descriptions thereof will be omitted.

The tanning apparatus 4 includes a controller (not shown), a body 100, a light source 20, and a sensor 30. The tanning apparatus 4 may further include an input unit 40 and an alarm (not shown).

The light source 20 includes a lower light source 210c and an upper light source 220c. At least one of the lower light source 210c and the upper light source 220c includes light emitting elements 217, and the light emitting elements 217 may include UV light emitting diodes LED1 to LED9 having different peak wavelengths. A portion of the light emitting elements 217 may constitute a light emitting unit 215b. The light emitting unit 215b according to the present exemplary embodiment may generally be similar to the light emitting unit 215b illustrated with reference to FIG. 9. The light emitting units 215b according to the present exemplary embodiment may be directly disposed in a light source installation space 115. It is contemplated that, however, various light sources 20 according to the exemplary embodiments may alternatively be applied thereto.

At least one of the lower light source 210c and the upper light source 220c may be divided into multiple light emitting regions that emit light having different luminous characteristics. For example, as shown in FIG. 12, the lower light source 210c may include a first light emitting region R1 and a second light emitting region R2. Each of the first light emitting region R1 and the second light emitting region R2 may include at least one light emitting unit 215b. Light emitted from the first light emitting region R1 may have different luminous characteristics than light emitted from the second light emitting region R2. For example, when a user wants different tanning results with respect to an upper body and a lower body, the different tanning results may be achieved by setting the first light emitting region R1 and the second light emitting region R2 to emit light having different wavelengths and luminous intensity.

Division of the light emitting regions illustrated with reference to FIG. 12 may be modified in various ways. For example, when the tanning apparatus 4 is used as a phototherapy apparatus, a user may designate a region of the skin suffering from skin disease or skin trouble and then input data, such that the light source emits light around the designated region. As such, the tanning apparatus or the phototherapy apparatus may provide an optimal tanning result to a user and/or local phototherapy, by utilizing the light sources 20 having multiple light emitting regions that may emit light having different luminous characteristics.

Figure 13:
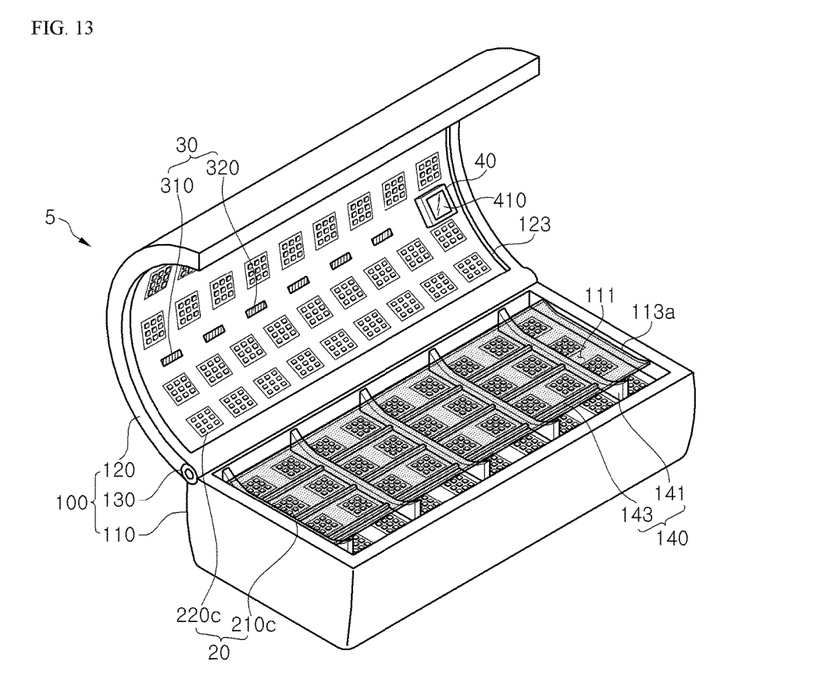
FIG. 13 is a perspective view of a tanning apparatus according to an exemplary embodiment of the present invention.

FIG. 13 is a perspective view of a tanning apparatus according to an exemplary embodiment of the present invention.

Unlike the tanning apparatus illustrated above with reference to FIG. 11, the tanning apparatus according to the present exemplary embodiment further includes at least one supporting element. Operations and constituent elements of the tanning apparatus 5 may be substantially similar to those of the tanning apparatus illustrated above, and thus, different features of the tanning apparatus 5 will be mainly described and repeated description thereof will be omitted.

The tanning apparatus 5 includes a controller (not shown), a body 100, a light source 20, a sensor 30, and a support element 140. The tanning apparatus 5 may further include an input unit 40 and an alarm (not shown).

The support element 140 may support a light source cover 113a. In this manner, the lower light source 210 and the light source cover 113a may be separated by a predetermined distance from each other. The support element 140 may be controlled to adjust heights thereof by a controller (not shown). A distance from a user to the lower light source 210c may be adjusted depending upon the height of the support element 140. Accordingly, the distance from a user to the lower light source 210c may be adjusted according to a desired tanning condition of the user, thereby providing optimal tanning effects.

The support element 140 may include a main support member 141 and a secondary support member 143. The main support member 141 and the secondary support member 143 extend in opposite directions so as to support the light source cover 113a. For example, the main support member 141 extends substantially parallel to a relatively short side of the tanning apparatus and the secondary support member 143 may extend substantially parallel to a relatively long side of the tanning apparatus, so as to intersect the main support member 141.

The light source cover 113a may have a rounded shape so as to form a concave upper surface. As shown in FIG. 13, the light source cover 113a may have a concave shape, such that a user may easily lie on the light source cover 113a. Accordingly, the support element 140 may have a shape corresponding to the concave shape of the light source cover 113a, so as to effectively support the light source cover 113a. For example, as shown in FIG. 13, the main support member 141 of the support element 140 may include an upper surface having a radius of curvature corresponding to the radius of curvature of the light source cover 113a.

Although certain exemplary embodiments and implementations have been described herein, other embodiments and modifications will be apparent from this description. Accordingly, the inventive concept is not limited to such exemplary embodiments, but rather to the broader scope of the presented claims and various obvious modifications and equivalent arrangements.

What is claimed is:

1. A tanning system, comprising:
   a light source comprising light emitting elements configured to emit ultraviolet (UV) light having different peak wavelengths;
   a controller configured to control luminous characteristics of the light source; and
   a sensor configured to sense at least one of the luminous characteristics of the light source and a user's skin condition, wherein:
the luminous characteristics of the light source are controlled by the controller based on the user's skin condition sensed by the sensor;
controlling the luminous characteristics comprises increasing or decreasing luminous intensity of one or more of the light emitting elements;
the sensor is configured to send data corresponding to the luminous characteristics of the light source sensed thereby to the controller; and
the controller is configured to determine defects in the light source based on the data corresponding to the luminous characteristics of the light source.

2. The tanning system of claim 1, wherein the luminous characteristics of the light source are controlled according to the user's skin condition sensed by the sensor and based on data previously input by the user.

3. The tanning system of claim 1, wherein the luminous characteristics of the light source comprise at least one of wavelengths of light emitted therefrom, luminous intensity depending upon wavelengths, luminous spectrum of light, and irradiation time of light.

4. The tanning system of claim 1, wherein the user's skin condition comprises at least one of skin color, melanin concentration, skin sebum, skin moisture, skin temperature, and skin trouble.

5. The tanning system of claim 1, wherein the sensor is configured to contact or be separated from the user during sensing the user's skin condition.

6. The tanning system of claim 1, wherein the light emitting elements of the light source comprise UV light emitting diodes.

7. The tanning system of claim 6, wherein:
the UV light emitting diodes are configured to emit UV light having different peak wavelengths that have a substantially constant interval therebetween; and
the controller is configured to control each of the UV light emitting diodes to increase or decrease luminous intensity thereof.

8. The tanning system of claim 1, further comprising:
an alarm controlled by the controller.

9. The tanning system of claim 1, wherein light emitted from the light source comprises about 95% or more of ultraviolet A (UVA) light.

10. A tanning apparatus, comprising:
a body comprising:
a tanning space; and
a support element disposed in the tanning space;
a light source configured to emit ultraviolet (UV) light to the tanning space, the light source comprising light emitting elements configured to emit UV light having different peak wavelengths;
a controller configured to control luminous characteristics of the light source; and
a sensor configured to sense at least one of the luminous characteristics of the light source and a user's skin condition,
wherein:
the luminous characteristics of the light source are controlled by the controller based on the user's skin condition sensed by the sensor;
controlling the luminous characteristics comprises increasing or decreasing luminous intensity of one or more of the light emitting elements; and
the support element is configured to protrude within the body to adjust a distance between the light source and a user.

11. The tanning apparatus of claim 10, further comprising:
an input unit.

12. The tanning apparatus of claim 11, wherein the luminous characteristics of the light source are controlled according to the user's skin condition sensed by the sensor and based on data previously input by the user.

13. The tanning apparatus of claim 10, wherein:
the light emitting elements comprise UV light emitting diodes configured to emit UV light having different peak wavelengths that have a substantially constant interval therebetween; and
the controller is configured to control each of the UV light emitting diodes to increase or decrease luminous intensity thereof.

14. The tanning apparatus of claim 13, wherein:
the light source has an elongated shape extending in one direction;
a portion of the UV light emitting diodes comprises a light emitting unit; and
the light source comprises multiple light emitting units.

15. The tanning apparatus of claim 14, wherein the light emitting units are disposed along an extending direction of the light source.

16. The tanning apparatus of claim 14, wherein the light emitting units are disposed along a direction different from an extending direction of the light source.

17. The tanning apparatus of claim 14, wherein:
the light emitting units are disposed at a substantially constant interval with respect to each other; and
a distance between light emitting elements of adjacent light emitting units is substantially the same as a distance between adjacent light emitting elements of the same light emitting unit.

18. The tanning apparatus of claim 10, wherein the light source comprises light emitting regions configured to emit light having different luminous characteristics.

19. The tanning apparatus of claim 10, further comprising:
an alarm configured to provide at least one of visual and audible signals to a user.

20. The tanning apparatus of claim 10, wherein the light source is configured to further emit IR light and/or visible light.

21. The tanning apparatus of claim 10, wherein the body further comprises:
a light source installation space receiving the light source therein; and
a cover unit covering the light source installation space.

22. A phototherapy system, comprising:
a light source comprising light emitting elements configured to emit UV light having different peak wavelengths;
a controller configured to control luminous characteristics of the light source; and
a sensor configured to sense at least one of the luminous characteristics of the light source and a user's skin condition,
wherein:
the luminous characteristics of the light source are controlled by the controller based on the user's skin condition sensed by the sensor;
controlling the luminous characteristics comprises increasing or decreasing luminous intensity of one or more of the light emitting elements;
the sensor is configured to send data corresponding to the luminous characteristics of the light source sensed thereby to the controller; and the controller is configured to determine defects in the light source based on the data corresponding to the luminous characteristics of the light source.

* * * * *